United States Patent
Larsen et al.

(10) Patent No.: US 7,262,844 B2
(45) Date of Patent: Aug. 28, 2007

(54) ULTRASENSITIVE SPECTROPHOTOMETER

(75) Inventors: David W. Larsen, St. Charles, MO (US); Zhi Xu, St. Louis, MO (US)

(73) Assignee: The Curators of the University of Missouri, Columbia, MO (US)

( * ) Notice: Subject to any disclaimer, the term of this patent is extended or adjusted under 35 U.S.C. 154(b) by 89 days.

(21) Appl. No.: 11/035,034

(22) Filed: Jan. 13, 2005

(65) Prior Publication Data

US 2006/0152726 A1 Jul. 13, 2006

(51) Int. Cl.
 *G01J 3/42* (2006.01)

(52) U.S. Cl. .................................. 356/319; 356/416

(58) Field of Classification Search ................ 356/319, 356/416
See application file for complete search history.

(56) References Cited

U.S. PATENT DOCUMENTS

| 3,877,817 | A | 4/1975 | Ralston |
| 4,059,405 | A | 11/1977 | Sodickson et al. |
| 4,070,111 | A | 1/1978 | Harrick |
| 4,213,703 | A | 7/1980 | Haunold et al. |

(Continued)

FOREIGN PATENT DOCUMENTS

JP 06053919 2/1994

OTHER PUBLICATIONS

Product Catalog 2003, Ocean Optics, Inc.

(Continued)

*Primary Examiner*—Gregory J. Toatley, Jr.
*Assistant Examiner*—Kara Geisel
(74) *Attorney, Agent, or Firm*—Sennniger Powers

(57) ABSTRACT

The invention concerns measurements in which light interacts with matter to generate light intensity changes, and spectrophotometer devices of the invention provide ultrasensitive measurements. Light source noise in these measurements can be reduced in accordance with the invention. Exemplary embodiments of the invention use sealed housings lacking an internal light source. In some embodiments a substantially solid thermally conductive housing is used. Other embodiments include particular reflection based sample and reference cells. One embodiment includes a prism including an interaction surface, a detector, a lens that focuses a prism beam output onto the detector, and a closed interaction volume for delivering gas or liquid to the interaction surface. Another embodiment replaces a prism with a reflective surface. Another embodiment replaces a prism with a scattering matte surface. Aspects of the invention identify noise-contributing components in spectrophotometry and realize noise levels very near the shot noise limit.

28 Claims, 9 Drawing Sheets

U.S. PATENT DOCUMENTS

| | | | |
|---|---|---|---|
| 4,518,700 A | 5/1985 | Stephens | |
| 4,565,447 A | 1/1986 | Nelson | |
| 4,781,456 A | 11/1988 | Nogami | |
| 4,823,168 A | 4/1989 | Kamahori et al. | |
| 4,848,904 A | 7/1989 | Sapp et al. | |
| 4,922,309 A | 5/1990 | Sekiwa et al. | |
| 4,929,078 A | 5/1990 | Harmon | |
| 4,931,660 A | 6/1990 | Mayer | |
| 5,029,276 A | 7/1991 | Buehler et al. | |
| 5,134,276 A | 7/1992 | Hobbs | |
| 5,376,783 A | 12/1994 | Vecht et al. | |
| 5,434,412 A | 7/1995 | Sodickson et al. | |
| 5,452,085 A * | 9/1995 | Fancy et al. | 356/326 |
| 5,540,825 A | 7/1996 | Yeung et al. | |
| 5,628,891 A | 5/1997 | Lee | |
| 5,680,209 A | 10/1997 | Machler | |
| 5,784,158 A * | 7/1998 | Stanco et al. | 356/326 |
| 6,741,348 B2 | 5/2004 | Larsen et al. | |
| 2002/0021441 A1 * | 2/2002 | Norton et al. | 356/326 |
| 2005/0012925 A1 * | 1/2005 | Saptari et al. | 356/319 |

OTHER PUBLICATIONS

Kurt L. Haller and Philip C.S. Hobbs, "Double Beam Laser Absorption Spectroscopy: Short Noise-Limited Performance at Baseband with a Novel Electronic Noise Canceller", SPIE, vol. 1435, Optical Methods for Ultrasensitive Detection and Analysis: Techniques and Applications (1991) pp. 298-309.

* cited by examiner

ULTRASENSITIVE SPECTROPHOTOMETER

TECHNICAL FIELD

The field of the invention is spectrophotometry. Devices and methods of the invention are applicable to all uses of spectrophotometry, i.e., the measurement of light absorption or scattering in liquids, gases and solids and at their interfaces. A wide range of spectroscopic and analytical instruments and devices may benefit from the invention. Exemplary applications of the invention include Ultra Violet—Visible (UV-Vis), Infrared (IR), Atomic Absorption (AA), circular dichroism (CD) spectrophotometers, and High Performance Liquid Chromatography (HPLC).

BACKGROUND ART

A fundamental property of a sample, be it gas, liquid or solid, is its tendency or lack of tendency to absorb or scatter light at certain wavelengths. Characterization of the tendency of a sample to absorb, scatter or transmit is the basis for spectrophotometry. Example applications include chemical and biological sample analysis. Other example applications include manufactured product testing and the testing of air or water quality.

The point of any application of quantitative spectrophotometry is the ability to numerically characterize a sample in order to discover sample properties or to differentiate it from another sample. Irrespective of the application, the critical aspects of quantitative spectrophotometry are sensitivity, precision, and accuracy. The sensitivity of a spectrophotometric measurement directly relates to the ability to detect small differences between samples having similar absorption properties. The greater the sensitivity, the smaller the difference that can be detected. The precision of a spectrophotometric measurement may be considered as a function of the ability to repeat the same measurement for an identical sample at different times. The accuracy of a spectrophotometric measurement may be considered as a function of the ability to correctly determine the numerical measure of the sample composition. The latter is critical, for example, when attempting to quantify an unknown element in a sample. Over a given range of concentration, the quantification is characterized by certain levels of precision and accuracy. However, below the lower limit of the concentration range, both precision and accuracy are adversely affected. This lower limit is the detection limit of the particular spectrophotometric instrument. As sensitivity increases, the detection limit decreases. Improvements in sensitivity, while retaining high levels of precision and accuracy are desirable.

We have previously provided for increased sensitivity in spectrophotometry that uses transmittance measurements. Our U.S. Pat. No. 6,741,348 (the '348 patent) discloses methods and devices that provide highly sensitive spectrophotometric measurements.

DISCLOSURE OF THE INVENTION

The present invention extends the measurement capabilities of the '348 patent to a range of other measurements in which light interacts with matter giving rise to changes in light intensity. Preferred embodiment spectrophotometer devices of the invention provide for ultrasensitive measurements through a reflection interaction with matter. The level of light source noise in these measurements can be reduced in accordance with the invention. Preferred embodiments of the invention use sealed housings lacking an internal light source, and reflection based sample and reference cells. In some embodiments a substantially solid thermally conductive housing is used. Devices of the invention use a dual light beam configuration with sample and reference beams. The dual beams are derived from the same light source, so that experimental noise associated with the light source, both relatively fast random fluctuation and slower drift, will appear coherently in both beams. A sensitivity increase is achieved in embodiments of the invention by reducing the level of the coherent experimental noise by use of a cancellation technique. Other features of preferred embodiments include particular reflection based sample and reference cells. A total internal refelection embodiment includes, for example, a prism including an interaction surface, a detector, a lens that focuses a beam output from the prism onto the detector, and a closed interaction volume having an inlet and an outlet for delivering analytes to the interaction surface. In a specular reflection embodiment, a reflective surface is used instead of a prism. In a diffuse refelection embodiment a matter surface is used instead of a prism. Aspects of the invention include identification of noise-contributing components in spectrophotometry and the select set of preferred features in a given embodiment, and noise levels very near the shot noise limit may be realized with application of preferred embodiment devices.

BRIEF DESCRIPTION OF THE DRAWINGS

Other features, objects, and advantages of the invention will be apparent to those skilled in the art by reading of the detailed description in view of the drawings, of which.

BEST MODE OF CARRYING OUT THE INVENTION

Figure 1:
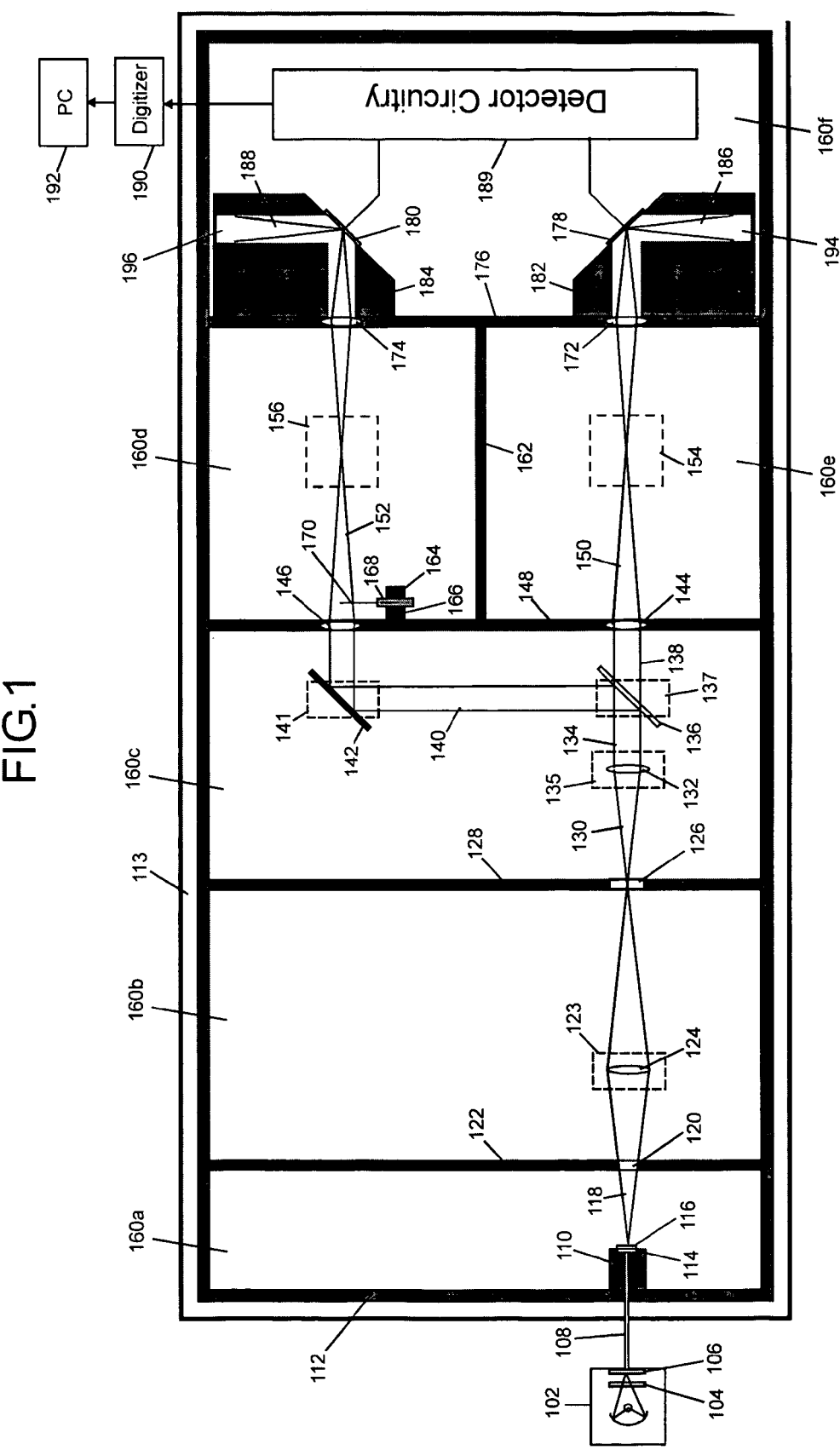
FIG. 1 is a top schematic view of a preferred embodiment spectrophotometer with its cover removed.

The invention is broadly directed to increased sensitivity in spectrophotometry. Broader aspects of the invention include identification of noise-contributing components in spectrophotometry and the select set of preferred features in a given embodiment. Some embodiments of the invention seek to realize this type of reduction by applying a combination of the aspects of the invention, i.e., individual solutions to all identified sources of noise. In these preferred embodiments, such a reduction will only be realized after all important sources of noise are identified and minimized. Preferred embodiments of the invention can produce noise levels very near the shot noise limit. Artisans will appreciate additional aspects of the invention by reference to the preferred embodiments.

The invention provides for measurements that address the potential interferences caused by airborne particulates in the beam paths, bubbles and suspended particulates in liquids under study, reflections from light detector surfaces, and others. Such noise sources have traditionally not been considered in conventional devices that were incapable of providing the sensitivity required to make such sources relevant.

Devices of the invention use a dual light beam configuration with sample and reference beams. The dual beams are derived from the same light source, so that experimental noise associated with the light source, both relatively fast random fluctuation and slower drift, will appear coherently in both beams. A sensitivity increase is achieved by reducing the level of the coherent experimental noise by use of a cancellation technique. The sample and reference beams induce photocurrents in sample and reference detectors, and the coherent fluctuations are canceled by taking the difference in sample and reference photocurrents ($I_S$–$I_R$) by use of appropriate electronic circuitry. The circuit outputs a difference voltage $V_D$ given by:

$$V_D = K_D(I_S - I_R) \quad (1)$$

$K_D$ is a constant of proportionality, which is determined by the parameters of the electronic circuitry. As the photocurrents $I_S$ and $I_R$ become identical, coherent random fluctuations of the light source, which are equally present in both beams, are canceled in the difference voltage $V_D$. While the effects of light source drift are cancelled in the baseline $V_D$, they do affect the peak height. To correct for this effect, $V_D$ is divided by the output reference voltage $V_R$ given by:

$$V_R = K_R I_R \quad (2)$$

$K_R$ is a constant of proportionality, which is determined by the parameters of the electronic circuitry. Source drift affects both $I_S$ and $I_R$ equally and it can be seen from equations 1 and 2 that source drift is canceled by dividing $V_D$ by $V_R$.

$$V_D/V_R = K_D/K_R[I_S/I_R - 1] \quad (3)$$

From equation 3, the ratio $I_S/I_R$ can be calculated:

$$I_S/I_R = V_D/V_R(K_D/K_R)^{-1} + 1 \quad (4)$$

Finally, the Absorbance A can be calculated from the experimental value of $I_S/I_R$ from the expression A=–log ($I_S/I_R$). Transmittance measurements are typically used for analyses of true solutions. In a true solution, the analytes are dispersed at the molecular level. True solutions are visibly clear so that no appreciable amount of light is scattered, e.g., by suspended particulates, and the reduction of the light intensity as it passes through the solution occurs primarily by absorption. With devices of the invention it is possible to measure the Absorbance of pure solutions with greatly improved accuracy and to use the Beer-Lambert Law to analyze data.

An example transmittance embodiment spectrophotometer is illustrated in FIG. 1, and will be used to describe some basic noise reduction aspects that apply to reflection embodiments disclosed in FIGS. 2-7. In the configuration of FIG. 1, which relies on transmittance, light passes directly through a sample, and light intensity is reduced by interaction with the sample. In the case of an optically clear sample, the reduction of light occurs by absorption as described in the patent. In transmittance measurements, light intensity can also be reduced because of the presence of suspended macroscopic structures that scatter the light. These suspensions typically appear cloudy and the method used for their analysis is called "turbidimetry." The mathematical relationship between the reduction in light intensity and the amount of analyte in suspension must obtained empirically. The Beer-Lambert Law may not apply. Nevertheless, the method is useful and is used routinely. Turbidimetry and other transmittance applications can also be implemented using the methodology of FIG. 1, and as described in the '348 patent.

A second general type of optical measurement is reflectance, and FIGS. 2-7 present exemplary devices that extend the principles that permit ultrasensitive transmittance measurements in the FIG. 1 embodiment to samples that are better interrogated with a reflection measurement. Separate embodiments are provided for internal reflectance, specular reflectance and diffuse reflectance, and artisans will understand broader aspects of the invention with reference to these embodiments.

We begin now with the transmittance embodiment of FIG. 1, which has been constructed as an experimental prototype. The spectrophotometer of FIG. 1 embodies multiple inventive aspects, including an identification of noise sources and methods for addressing noise sources. The overall embodiment provides a useful framework to illustrate aspects of the present invention, which artisans will understand are broader than and applicable outside of the FIGS. 2-7 preferred embodiments. The FIG. 1 preferred embodiment device, for simplicity of illustration, is a single wavelength, filter unit that operates in the visible range with an Incandescent source (Tungsten lamp).

The general beam path in the FIG. 1 preferred embodiment is the typical dual beam configuration used for spectrophotometry. Light from a source 102, e.g. a Tungsten lamp, passes through two broad band optical filters 104, 106 and is carried by a light guide 108, preferably a fiber optic cable to the instrument. The light guide 108 has a low thermal conductivity, to avoid heat transfer from the light source into the device and is attached via a sealed mount 110. The mount 110 is sealed to prevent dust and stray light from entering the housing. The mount 110 is directly attached to an interior surface of housing wall 12.

This serves to isolate the light source 102. The particular choice for the type of light source will depend upon the specific application. The invention can be implemented over the entire spectral range from the UV to the Far IR, and the light source may be chosen as appropriate. Additional exemplary suitable light sources include the following: argon lamp, xenon lamp, hydrogen lamp, deuterium lamp, tungsten lamp, arc lamp, hollow cathode lamp, Nernst glower, nichrome wire, globar, lasers. The light source 102 is made external as a means of thermal isolation from other components of the preferred embodiment spectrophotometers.

The light source is usually capable of creating significant heat that can be transferred into the optical and detector portions of the spectrophotometer. The hot light source 102 is external to minimize conductive heat transfer to the instrument, allowing convective heat transfer into the surrounding environment instead. In addition, a thermal insulation layer 113 minimizes heat transfer from the surrounding environment to the preferred spectrophotometer. The filters 104 and 106 preferably include both ultraviolet and infrared cutoff filters to narrow the energy range of transmitted light so that "cold" light is produced and heat transfer by radiation is limited.

The preferred fiber optic light guide 108 has a polarization ratio that is sensitive to position and curvature of the fiber core. The guide fiber optic cable 108 is attached to mount 110, which contains a holographic diffuser 114 to reduce polarization, and aperture 116 to reduce the actual source diameter to a size, e.g., ⅛" for better collimation and focusing.

An emergent beam 118 passes through a second aperture 120 in a wall 122 and is collected and refocused by a double convex lens 124 configured with a 1:1 conjugation ratio. After passing through an interference filter 126 in a wall 128, a narrow band emergent beam 130 passes through a plano-convex collimation lens 132, which produces a collimated beam 134. The diameter of the collimated beam 134 is designed to be smaller than the open optical aperture of lenses 144 and 146. The lenses 124 and 132 are held in commercial optical holders mounted on thermally conductive mounts 123 and 135, respectively. The mounts have a large thermal capacity. A solid metal block is preferred for these mounts.

A dielectric beam splitter 136 produces, along separate paths, a transmitted (Sample) beam 138 and a reflected (Reference) beam 140, which is further reflected by a mirror 142. Beam splitter 136 is held in a brass holder fabricated by us and mirror 142 is held by a commercial adjustable holder, supported by optical mounts 137 and 141, respectively. These mounts have similar structure to mounts 123 and 135, with large heat capacity. The dielectric beam splitter 136 has a beam splitting ratio that is sensitive to the polarization of the incident beam 134. For example, for a dielectric beam splitter with average 60% transmission and 40% reflection, the transmission is only 42% for s-polarized light but is 76% for p-polarized light. Light emerging from a monochromator or optical fiber is partially polarized and the polarization ratio is subject to thermal and mechanic drift. In an exemplary experimental prototype of the invention, the optical fiber 108 had ⅜" core diameter. The polarization ratio is very sensitive to the position and curvature of the fiber core. Changes in the room temperature can easily cause changes in the relative differential voltage ratio $V_D/V_R$, which is a measure of the imbalance between the two beams, of order $10^{-5}$ or larger. Passing the light emerging from the fiber optic through the holographic diffuser 114 reduces the polarization ratio by a factor of 100. Thus, the polarization is essentially completely scrambled and the beam splitting ratio is much less susceptible to thermal drift so that differential stability is increased. The inventors also found that a traditional glass diffuser with roughened surface is not effective because it does not provide sufficient polarization scrambling.

The sample 138 and reference 140 beams pass through focusing lenses 144 and 146 in a wall 148, and focused beams 150 and 152 enter a sample cell 154 and a reference cell 156, respectively. The sample cell 154 is in a compartment 160e and the reference cell in a compartment 160d. The two chambers are separated by a wall 162. The balance of the beams is facilitated by the overall thermal stability features of the preferred embodiment, and the optical system in general, including the dielectric beam splitter 136. To help balance the two beams, the power of the reference beam 152 can also preferably be attenuated by adjusting a high precision optical attenuater 164. The attenuator includes a mount 166, a precision michrometer-type screw 168 and a thin rod 170. The beams continue through focusing lenses 172 and 174 mounted in a wall 176 and are collected by detectors 178 and 180, which are mounted in thermally conductive chambers 182 and 184, respectively. The detectors are preferably mounted at 45° angles to the incident light directions within chambers 182 and 184. Thus, light beams 186 and 188 reflected by the detector surfaces remain trapped inside the chambers in light traps 194 and 196, respectively. The photodiode detectors produce photocurrents, which are fed to a detector circuit 189. An appropriate detector will produce a current that varies in precise proportion to the power of an impingent (sample or reference) beam. Alternative potential detectors include, for example: photomultipliers, phototubes, photocells, charge transfer conductor, thermocouples, bolometers, pyroelectric cells, and infrared detectors. The circuitry produces output voltages, which are fed through the housing 112 to a digitizer 190 and analysis circuit 192, realizable, for example, with a computer.

A thermally conductive circuit is established among internal components through a base (not shown) having a large thermal capacity. In an experimental prototype constructed in a accordance with a transmissive arrangement shown in FIG. 1 of the '348 patent, the base was ¾ inch solid steel and mounts/cells 123, 135, 137, 141, 154, and 156, and the various walls and outer housing were attached directly thereto. The base and an unshown top cover and the housing outer wall 112 form a conductive heat transfer circuit with internal components. The cover, base and wall 112 are insulated from the environment, for example, with ½ inch commercial installation 113. This slows the response of internal temperature to a change in the outside environment. The internal thermal conductivity promotes equilibrium among internal components.

Figure 2A:
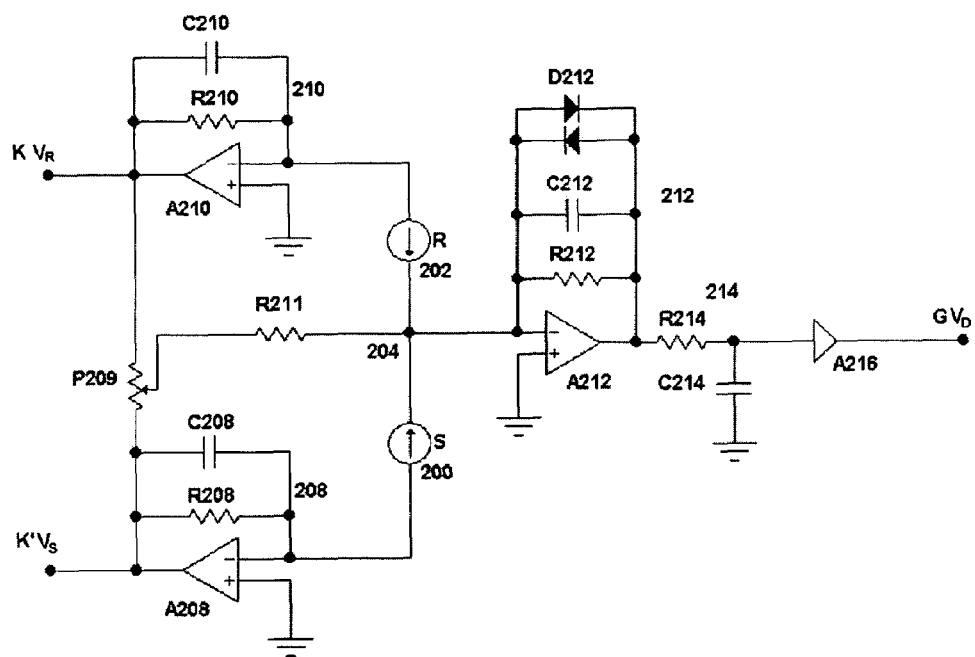
FIGS. 2A, 2B and 2C illustrate preferred embodiment detector circuits.

A preferred embodiment detector circuit is shown in FIG. 2A. An exemplary experimental prototype circuit according to the preferred FIG. 2A (top) embodiment was made with inexpensive, commercially available components.

In FIG. 2A, currents from the Sample (S) and Reference (R) photodiodes 178 and 180 (FIG. 1) are represented as constant current sources 200 and 202, respectively. The photodiodes are configured so that the difference in their photocurrents appears at a node 204. A converter 208 (including A208, R208, and C208) converts the S photocurrent 200 to a voltage, which is fed to one end of a potentiometer P209. A converter 210 (including A210, R210, and C210) converts the R photocurrent 202 to a voltage, which is fed to the other end of the potentiometer P209. The output voltage from converter 208 is negative, while that from converter 210 is positive, so the full voltage difference is dropped across P209. This voltage will follow the DC power of the light source, and it will also contain noise and drift components of the light source. The polarity and magnitude of the output voltage from P209 varies with the position of the potentiometer. For example, voltage can be varied continuously from K $V_R$ (which is positive) through zero to K' $V_S$ (which is negative). The constants are K=R212/R210, and K'=R212/R208. This voltage from P209 is fed back as a current through a feedback resistor R211 to the node 204. The feedback current precisely tracks the light source power, and its magnitude and polarity is determined by the values of several components (R208, R210, P209 and R211). Thus, addition of this feedback current to node 204 has the effect of increasing the magnitude of either the S photocurrent or the R photocurrent, depending upon the setting of P209. With this provision, careful adjustment of the feedback current by use of potentiometer P204 allows the S and R photocurrents to be balanced so that the source noise can be cancelled to a high degree. If the S photocurrent is greater than the R photocurrent, P209 is adjusted to give the required positive voltage output, and vice versa. Component values are chosen to make the feedback current of suitable size to allow the S and R photocurrents to be balanced. Required feedback currents can be less than 1% of the S photocurrent, and a very small degree of photocurrent imbalance (e.g., $10^{-5}$) can be readily attained. Because the degree of source noise cancellation equals the degree of photocurrent imbalance in the circuit, $10^{-5}$ imbalance is more than sufficient to allow detector shot noise performance to be attained. A $10^{-3}$ photocurrent imbalance is sufficient to ensure shot noise limited performance.

For measurements at a single wavelength, the detector currents must be first balanced with solvent in both Sample and Reference cells. Following this, a measurement is made with analytical sample in the Sample cell. Since the balancing need be done only once, P209 can be a simple potentiometer as shown in both FIGS. 2A. and 2B. However, for Absorbance measurements made over a range of wavelengths, as with a scanning unit, the detector currents must be balanced at multiple wavelengths, with solvent in both Sample and Reference cells. This will in general require a different setting of P209 at each wavelength, so that when the spectrum is scanned with the analytical sample in the Sample cell, the setting of P209 will have to be changed prior to measuring each data point in the scan. Each P209 setting will correspond to the value that ensures balance at that particular wavelength. To accomplish this, P209 can be replaced with a computer controlled digital potentiometer, with the settings for every wavelength stored in memory.

In the balance condition, the total current at the input of a difference amplifier 212 approaches zero and source noise cancellation is achieved. The source noise cancellation is done in the current mode at node 204 so that S and R photocurrents are directly subtracted. The difference is then converted to an output voltage at the difference amplifier 212 (including A212, R212, C212, and D212). This is the simplest and most accurate method. The output of the difference amplifier 212 is fed through a low-pass filter 214 (including R 214 and C214) to an additional voltage amplifier 216 with gain G to produce and output difference voltage G $V_D$. The standard deviation of output G $V_D$ is determined by the shot noise of the detectors, not by the source noise as described above.

Figure 2B:
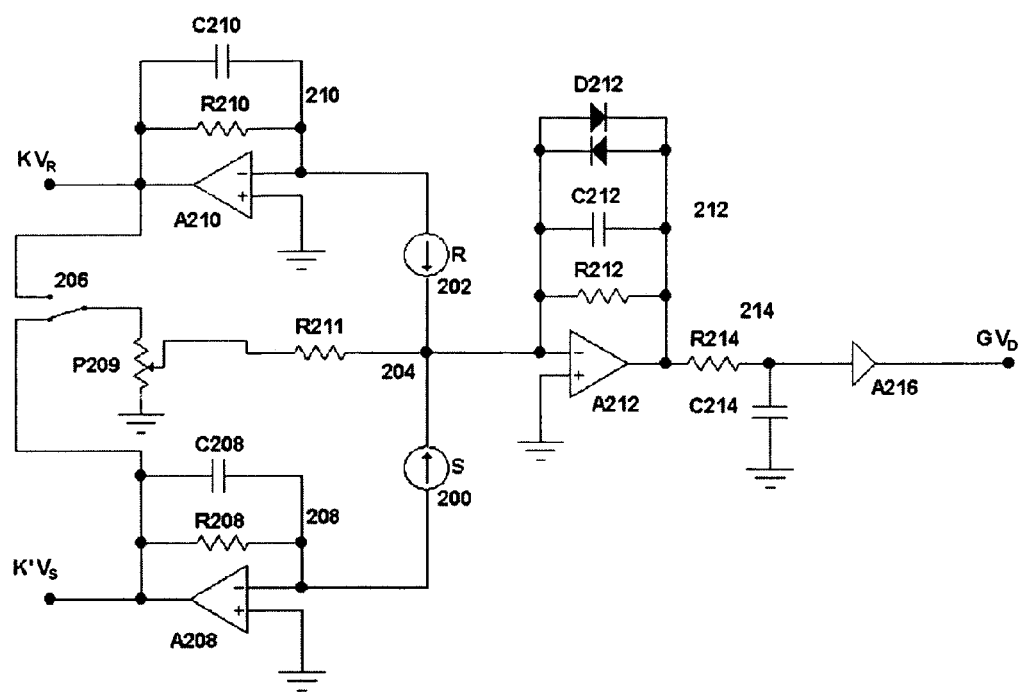
Figure 2C:
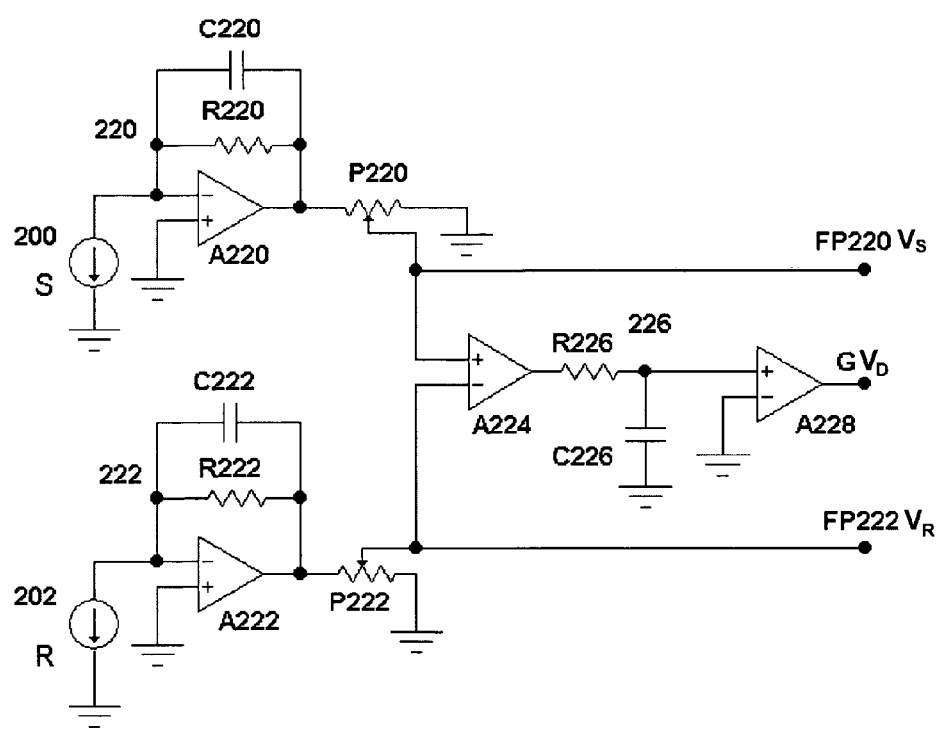

In FIGS. 2A and 2B, source noise cancellation is accomplished in the current mode. Alternatively, cancellation can be accomplished in the voltage mode. A preferred embodiment voltage mode noise cancellation detector circuit is shown in FIG. 2C. The source photocurrent from photodiode 200 is converted to a voltage by converter 220 (including A220, R220 and C220). The output voltage $V_S = I_S$ R220 is fed to a variable potentiometer P220, and the potentiometer output is fed to the non-inverting input of amplifier A224. Similarly, the reference photocurrent from photodiode 202 is converted to a voltage by converter 222 (including A222, R222 and C222). The output voltage $V_R = I_R$ R222 is fed to a variable potentiometer P222 and the potentiometer output is fed to the inverting input of amplifier A224. With the configuration shown in FIG. 2C, both $V_S$ and $V_R$ are positive. Thus, noise cancellation is implemented when the voltages at both inputs to amplifier A224 are equalized. Equalization can be done by first setting both P220 and P222 to maximum settings so that there is no voltage attenuation. Then, the potentiometer corresponding to the larger output voltage $V_S$ or $V_R$ is adjusted until the output of amplifier A224 is nulled. For example if $V_S < V_R$, P220 will normally be set at maximum, corresponding to FP220=1 and P222 will be adjusted for balance, corresponding to FP222<1. FP220 and FP222 are the fractional attenuations of the potentiometers, which range between 0 and 1. Coherent source noise is then cancelled in the voltage difference output by amplifier A224. The output of A224 is fed through a low pass filter 226 and finally output by buffer amplifier A228. With voltage cancellation, the voltage difference is defined as $V_D =$ (FP220 $V_S$ − FP222 $V_R$) and the output voltage is G $V_D$, where G is the composite gain of amplifiers A224 and A228. Voltage outputs FP220 $V_S$ and FP222 $V_R$ are also available. One of these outputs is required for the calculation of Absorbance as described below.

For measurement of large Absorbance values, noise cancellation is not required and the Transmittance can be obtained from the outputs of the 208 and 210 directly. For large Absorbances, diodes D212 limit the voltage output for difference amplifier 212. This controls interference relating to drift in the output of the difference amplifier 212. In experimental prototype devices, we have observed that, for a period of time after the difference amplifier produces an output of the order of volts, it is subject to drift, and this interferes with the accurate measurement of small $V_D$ values at output 216.

For $|V_R| > |V_S|$, Absorbance determination requires measurement of $Q = V_D/V_R + 1$ and for $|V_R| < |V_S|$, Absorbance determination requires measurement of $Q = [1 - V_D/V_S]^{-1}$. $V_D$ is available as the output voltage of 216 divided by G, the gain of the amplifier 216, $V_R$ is the output of 210 divided by the factor K, and $V_S$ is the output of 208 divided by the factor K'. $V_D$, $V_S$ and $V_R$ are available as separate output voltages so that $V_D$ and either $V_R$ or $V_S$ can be measured simultaneously, which is necessary to avoid error attributable to source drift. Source power drift must be considered because both $V_D$ and $V_R$ (or $V_S$) are directly proportional to source power. If $V_D$ and $V_R$ (or $V_S$) are not measured simultaneously, their ratio will vary as the source power changes between the times of measurement of the two voltages. However, with simultaneous measurement, the source power dependence cancels.

For the voltage cancellation circuit shown in FIG. 2C, Q can always be defined as $Q = V_D/$FP222 $V_R + 1$. The fractional attenuation FP222 is a constant and the quantity FP222 $V_R$ can be taken as the effective output of amplifier A222.

The correction performed in the detector circuit is aided by an optical balance, which can be positioned in either the Reference or Sample beam, or in both beams. The overall design of the optics should assure a near balance in the beams. A preferred feature also introduces a balance adjustment to fine tune the beam balance. If the beams are near balance in the overall design of the unit, there are two preferred means to adjust the degree of balance. First, there is a wall-mounted attenuator 164 (FIG. 1) that can impinge in the reference beam path to attenuate the reference beam. In the exemplary protoype, a wall mount 166 mounts a ¼-40 machine screw 168. The screw 168 was mounted near the edge of the beam, on an axis perpendicular to the beam direction. The end of the screw is turned down to a small rod 170, 1 mm diameter by 5 mm length. The position of the fine rod can be accurately adjusted with the fine screw thread. This screw, which provides a relatively coarse adjustment, can be used to balance the photocurrents $i_S$ and $i_R$ to about 1 part in $10^3$. Second, the photocurrent input to 212 (FIG. 2) can be nulled electronically by adjusting potentiometer P209 (FIG. 2), as described above. With the electronic adjustment capability, the photocurrents can be balanced to better than 1 part in $10^5$. By making the time constants of the feedback loops similar to the rise time of the detectors, tracking error in the small balance current is minimized. Except for the very small amount of current (<2%) supplied through R211, none of the current from either detectors is subject to electronic filters which could attenuate the high frequency components of the source noise. This ensures the fast response required for accurate noise cancellation. In addition, the main bulk of the detector currents does not flow through any electronic components. Finally, by making resistor R211 fairly large, additional noise produced because of its presence in the input circuitry of the difference amplifier will also be very small, experimentally found to be below the detector shot noise. The output of the difference amplifier 212 can be made small, of the order of 10 µV, by accurately balancing the beams electronically.

The circuit shown in FIG. 2A is suitable for use with a scanning instrument, where the light wavelength is continuously varied while taking data. Prior to making the measurement at each discrete wavelength, the beams must be balanced as described above. Since the relative powers of the Sample and Reference beams are expected to change over the wavelength range scanned, the ability to change the sign of the feedback current is a desirable feature, which is included in this circuit. A second preferred embodiment detector circuit is shown in FIG. 2B, where common components are labeled using the FIG. 2A reference numerals. This circuit is suitable for use with a unit operating at a single wavelength, as with a filter instrument. With this type instrument, it is not necessary to change the sign of the feedback current, since the measurement is made at only one wavelength. In FIG. 2B the balance current, derived from either the Sample or the Reference, is selected by a switch 206, so that only a single polarity current is available at any given time, depending upon the setting of the switch 206.

Our laboratory studies resulted in a discovery that after the source noise is cancelled thermal drift becomes dominant. Accordingly, another aspect of the invention is limiting thermal drift in the differential light power ratio. Preferably, thermal drift in the differential light power ratio, $\Delta P/P_R = (P_S - P_R)/P_R$ is limited to below $10^{-6}$ during the data acquisition period, which could be as long as 15 min in certain practical applications of the invention or aspects thereof. The relative differential voltage ratio $V_D/V_R = (V_S - V_R)/V_R$ is the experimental measure of $\Delta P/P_R$, so that what is of concern experimentally is differential voltage stability. A number of design features were identified and selected to limit thermal drift and to assure a high degree of differential stability. In particular, we sought to reduce temperature drift so that thermally induced changes in $V_D/V_R$ in the first embodiment will be of the order $10^{-6}$ or less over the measurement interval. This is consistent with overall noise at the detector shot noise limit. The preferred selection of identified factors given below become important when it is desired to measure light power changes on the order of $10^{-6}$. Since these factors have little impact on one's ability to detect power changes of order $10^{-4}$ or larger, the importance of thermal stability has not been generally appreciated. The analysis of thermal drift requires use of a number of thermal coefficients. Literature values were used for thermal coefficients when available; otherwise reasonable estimates of the coefficients were made by us. In some cases, the required coefficient was obtained by direct measurement. A first aspect of this portion of the invention involves the selection of components to address in the optimization of practical spectrophotometers according to the invention.

The beam splitter 136 is the most likely optical component for producing differential instability. In addition to the polarization of the incident beam 134, the splitting ratio is also very sensitive to the angle of incidence and the wavelength of the light. The incident angle dependent of $V_D/V_R$ is $6 \times 10^{-3}$ per degree. This means that a change in the angle of incidence of only 0.001 degree will cause $V_D/V_R$ to change about $6 \times 10^{-6}$. Such a small change in the angle of incidence could easily occur due to temperature induced expansion and twist of the beam splitter holder. The magnitude of any change that actually occurs will strongly depend on the structure and material of the beam splitter mount. The relatively large mount 137, made from a solid steel block provides both thermal and mechanical stability. A beam splitter holder in a transmittance experimental prototype was ½" thick brass plate, 3" high and 3" wide.

The interference filter 126 used in the exemplary experimental prototype had a temperature coefficient of 0.023 nm/° C., while the wavelength dependence of the differential ratio $V_D/V_R$ is $5 \times 10^{-4}$/nm for the dielectric beam splitter 136. This gives a composite coefficient of $1 \times 10^{-5}$/° C.

Temperature changes will also cause changes in the reflectivity of the beam splitter 136 which in turn have a minor effect on $V_D/V_R$, about $6.2 \times 10^{-6}$/° C. at a 45° angle of angle of incidence. This is caused by temperature induced changes in the refractive indices of the optical materials used.

Temperature changes will also cause the dark current of the two detectors 178 and 180 to change. Because of the configuration of the preferred embodiment detector circuit in FIGS. 2A and 2B, the dark currents of the detectors 178 and 180 tend to cancel. Detectors are preferably matched because mismatched detectors can reduce the cancellation effect. In the case of a severe mismatch, residual dark current could be as large as 150 pA. The temperature coefficient of the dark current is 115%/° C., which could translate to as much as 172 pA/° C. in the differential dark current. In the exemplary experimental embodiment, photocurrent is in the order of 2.0 µA. Therefore, the detector dark current creates a potential drift rate of $8.6 \times 10^{-5}$/° C. in the relative differential voltage ratio $V_D/V_R$.

An optimization goal for preferred embodiment designs was set forth based upon experimental observations, and by considering that a reasonable time is needed for making a measurement (up to 15 min). The inventors estimate that the maximum allowable thermal drift rate consistent with a measurement of $1 \times 10^{-6}$ AU is approx. 0.001° C./min. Temperature drift rates at or below this level may be achieved in accordance with preferred embodiments shown in FIGS. 1-7.

Another aspect of the invention is thermal stabilization of components. Primary passive thermal stabilization in embodiments of the invention has two aspects. Within the housing, components are made from materials having a high thermal conductivity, e.g., solid aluminum, steel, brass and other metals. Heat transfer among internal components promotes thermal equilibrium within embodiments of the invention. Insulation against outside environments is another aspect, which protects the instrument against changes in the surrounding environment by slowing a device's response thereto. A thick base plate having a large thermal capacity is provided, e.g., a thick base plate made of ¾ inch stainless steel plate, as a foundation for heat transfer among internal components. Bulky metal optical mounts also provide a large thermal capacity and great mechanical stability. Mounts of solid steel blocks approximately ¾" thick mounted directly to the base plate can contribute to stability and, for example, the entire housing may be thermally shielded with a layer of ½ inch commercial insulation material.

Figure 6:
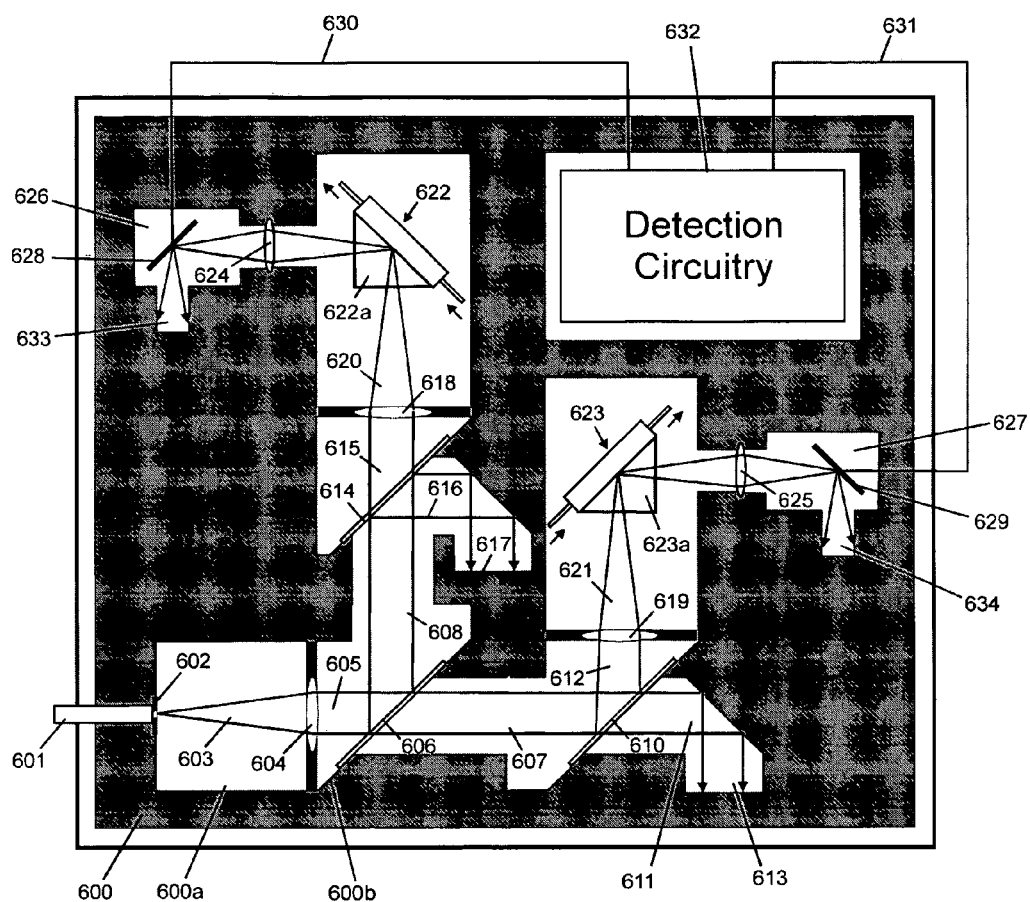
FIG. 6 is a top schematic view of another preferred embodiment total internal reflection spectrophotometer with its cover removed.
Figure 7:
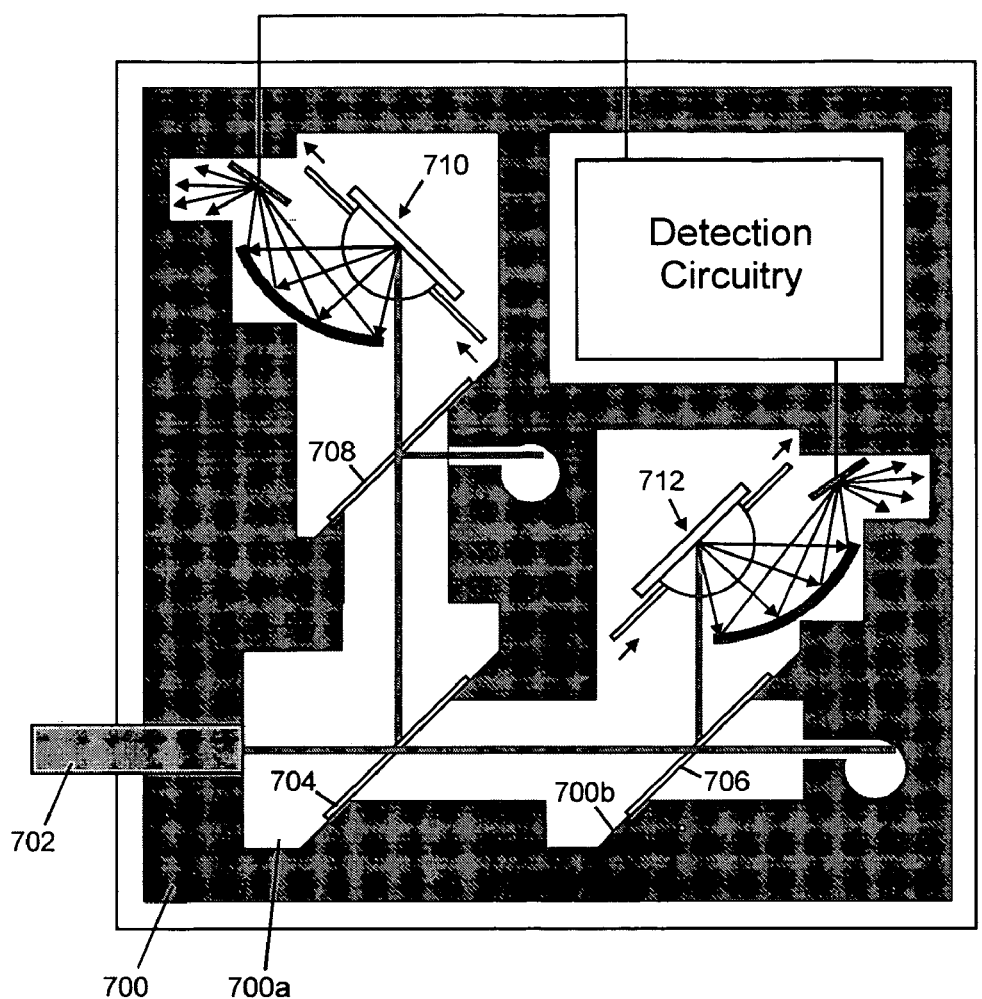
FIG. 7 is a top schematic view of another preferred embodiment diffuse reflection spectrophotometer with its cover removed.

Compartmentalization in preferred embodiments accomplishes multiple benefits that lead to reduced susceptibility to thermal drift, either directly or indirectly. Compartmentalization allows some of the optical components to be mounted on housing walls, which provides good thermal contact and stability. Walls 122, 128, 148, 162, and 176 facilitate this goal in the FIG. 1, 3-5 embodiments. In the embodiments of FIGS. 6 and 7 good thermal contact and stability is achieved with a unitary and substantially solid housing. Second, it allows the sample and reference cell to be optically isolated, which minimizes problems associated with stray light. In addition, the interior surfaces of the walls and housings are preferably coated with a light absorbing material, e.g., matte black paint.

Lenses, filters, and mirror, e.g., 114, 124, 126, 132, 142, 144, 146, 172, and 174, are configured to be resistant to variation of performance due to temperature change. The mounts for optical components are solid and bulky.

The large size is to ensure stability against thermal expansion. A holder for the beam splitter may be made quite massive, e.g., three inch square and ½ inch thick solid metal, to minimize potential thermal drift. Differential drift caused by the beam splitter can be made, for example, below $1\times10^{-6}$ over a 15 min. period or $6.7\times10^{-5}/°$ C.

A typical silicon photodiode detector may possess a reflectivity near 20% in the visible region (400-750 nm). Trapping reflected light from the detector surfaces has been determined to be beneficial. Light propagating back toward the sample holder 154 or the reference holder 156 can lead to undesired reflection and scattering. If reflected light is allowed to propagate back toward the sample or reference cell holders 154 and 156, multiple reflections can be created between the surfaces of cells, lenses, and detectors. With multiple reflections, any small thermal change resulting in repositioning of any of these components could have an effect that prevents detection of light changes at the $10^{-6}$ level. The reflection from the detector surface is controlled in the transmittance embodiment to address this problem. The preferred manner of reflection control includes aligning the surfaces of the sample detector 178 and reference detector 180 at an angle that is not perpendicular to the incident beam.

In preferred embodiments, the angle of incidence on the detector is 45° so that the propagation direction of the reflected light is 90° to the incident beam. The chambers 182 and 184 for the detectors mount the detectors at an angle to direct reflected light beams 186 and 188 into respective light traps 194 and 196. Any angle between a lower limit sufficient to direct the light into a light trap and an upper limit that allows all the light to be collected by the detector may be used. The values for these limits will be determined by the cross sectional areas of the light beam and detector. The reflected light 186 and 188 is trapped by the light traps 194 and 196, the inside surfaces of which are painted black. Trapping the reflected light by the detector surface is believed important for the determination of Absorbances below $5\times10^{-5}$ AU.

Any type of contaminant or particulate in the paths of the beams through the sample or reference will cause an interference. As used herein, contaminants and particulates have been identified to include, for example, bubbles, dissolved gases, and dust. For example, if the beam cross-section in the sample region is about 5 mm$^2$ (as in the exemplary prototype according to the first embodiment), then any particle with cross-section larger than 5 μm$^2$ or a diameter larger than 2.3 μm could cause a noise peak greater than $1\times10^{-6}$ AU. We found in our investigations that problem-causing airborne particles usually settled to the bottom of the sample chamber within 20 minutes after closing the chamber. The presence of airborne dust particles in a sample beam manifests itself in a series of positive-going sharp spikes in the detector signal. The dust peaks tend to decrease with time as the particles settle. For particles in liquids, on the other hand, it usually takes several hours for particles to settle to the bottom of the cell because of Brownian movement. In addition, any temperature change will tend to reactivate their movement across the entire liquid cell. This is a serious problem for detection of very small Absorbances in liquid samples. In our testing, these particles can easily cause a noise as high as $5\times10^{-5}$ AU.

Figure 3:
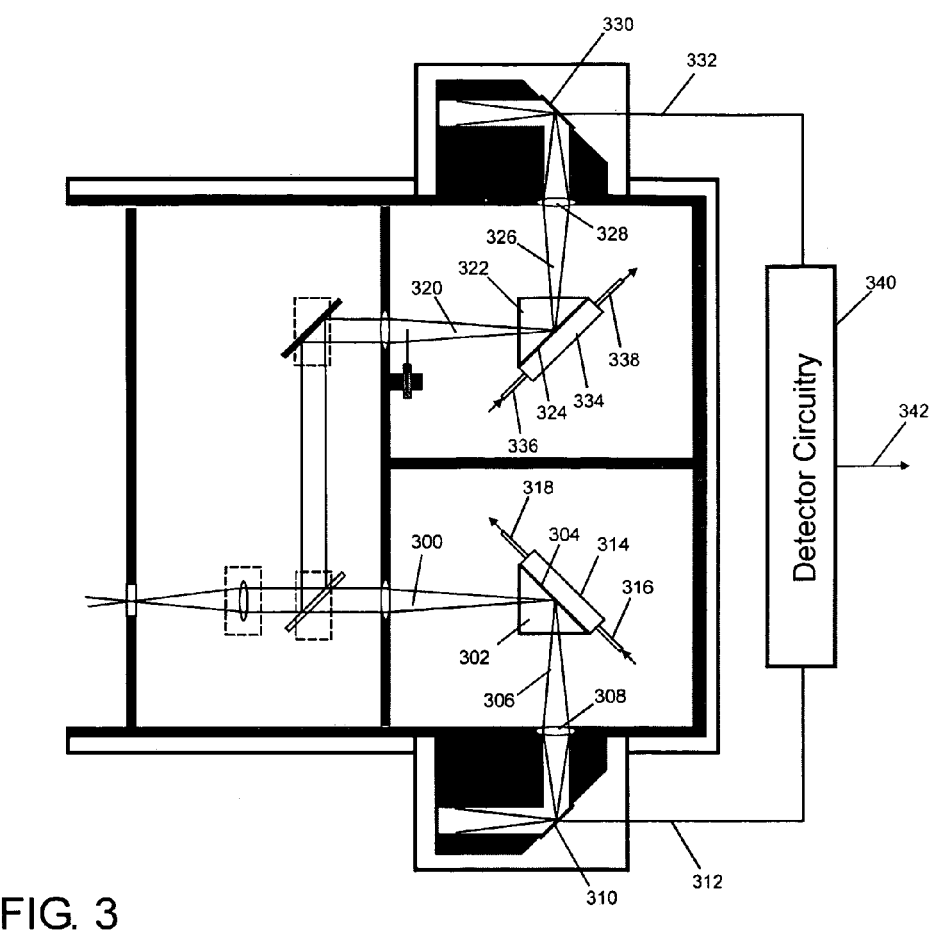
FIG. 3 illustrates a portion of a preferred embodiment total internal reflection spectrophotometer.

In tests, it was determined that due to dust in the air, the traditional cuvette structure with stopper is not suitable for determination of Absorbances below $5\times10^{-5}$ AU, because dust particles will tend to enter the cuvette anytime during the process of washing the cell or changing the liquid. Furthermore, opening the sample cell will tend to introduce airborne particles into the optical system. A solid metal body bored out to create the necessary liquid flow channels and openings is preferred. The inventors also identified additional potential noise sources in addition to the dust problem. For example, it was determined that the temperature of the liquid under study may be different from that of the cell by several degrees. Commonly used quartz cells exhibit relatively small heat conductivity and accordingly often need five minutes or longer for the temperature of the liquid to stabilize. Another aspect of the invention addresses potential noise from dust/particulates and variation of cell temperature Example embodiment reflectance measurement methods and devices are based upon a modification of the FIG. 1 embodiment. FIG. 3 shows a modified portion of the FIG. 1 embodiment, in which transmission cells 154 and 156 are replaced so that internal reflectance measurements may be made. This requires different cells, and also a reposition of the detectors.

In FIG. 3, a sample beam 300 enters an internal reflectance optical device, e.g., a prism 302 or other internal reflection optical device. The beam travels through the prism 302 and strikes an interaction surface 304, at which it undergoes a total internal reflection, so that the beam 306 passes out of the prism 302. The beam direction is changed by 90° in this case, but this angle is used as an example only and other direction changes may be used. The reflected beam 306 is focused by a lens 308 onto a sample detector 310 mounted in a chamber including a light trap 311 in the fashion (non-perpendicular) as described with respect to FIG. 1. An analyte (sample) is at or on the interaction surface 304 of the prism, and as the light beam undergoes the total internal reflection at the surface 304, the light, in essence, penetrates a very small distance into the analyte (the so called evanescent wave). The penetration depth is approximately equal to the wavelength of the light. Because the light penetrates the sample, the intensity of the light beam will be reduced by absorption or other interaction with the sample on surface 304. The extent of the intensity reduction depends on the chemical nature of the sample and can be used for analyte quantification. Sample is delivered to the surface 304 with a closed sample volume 314 having an inlet 316 and an outlet 318, both of which are connected to the exterior of the housing to allow an analyte sample to be introduced into the sample cell without the need to open the entire housing, which introduces baseline noise associated with airborne dust particles.

In similar fashion to the sample beam, a reference beam 320 enters a prism 322 and is reflected off a prism interaction surface 324. An emergent beam 326 is focused by lens 328 onto a reference detector 330, e.g. a photodiode, housed in a chamber including a light trap 331 and mounted at a non-perpendicular angle. The reference substance is contained in a closed interaction volume 334 fitted with inlet 336 and outlet 338 ports. The nature of the interaction between the reference beam and the reference substance at the reference interaction surface 324 is identical to that occurring at the sample interaction surface 304.

Signals from sample and reference detectors 310 and 330, respectively are fed via signal lines 312 and 332 into a detector circuit 340, which in exemplary embodiments is constructed in accordance with the detector circuits of FIG. 2A or 2B. Source noise cancellation is accomplished in the detector circuit 340 by taking the difference between the outputs of the sample detector 310 and the reference detector 330. The cancellation requires that the sample and reference photocurrents be balanced, and that absorption of light attributable to the analyte be measurable. This is readily accomplished and will be illustrated with a following example.

For simplicity, we assume that it is desired to analyze a two-component gas mixture. The primary component gas is present in large excess and the secondary component gas is present in trace amount. The trace gas is called the analyte and it is of interest to quantitate the analyte. The two-component gas sample mixture is placed in the sample interaction volume 314 and the pure primary gas is placed in the reference interaction volume 334. Under these conditions, if the primary gas absorbs light, the amount of gas absorption will be essentially the same from both sample and reference substances. In addition, the amounts of light reflected from the interaction surfaces of prisms 302 and 322 and absorbed by the bodies of these prisms will be the same for both sample and reference beams. Thus, the photocurrents in both sample and reference detectors, 310 and 330, respectively, will remain balanced except for the analyte absorption. Thus, primary gas absorption and prism absorption/reflection effects are cancelled so that analyte quantitation is possible. Also, because the photocurrents remain essentially balanced, source noise cancellation is accomplished. Without primary gas in the reference compartment 334, there will be absorption effects from both primary and analyte gases in the signal from the sample detector 310, and the absorption from the primary gas will need to be determined in a separate experiment. In addition, maintaining photocurrent balance will be more complicated without the proper primary gas reference. For liquid analyte samples, the prisms 302 and 322 are modified to allow for a much larger internal reflection angle than 90°, which then necessitates additional optics or the re-positioning of the detectors 310 and 330 so the detectors receive the reference and sample beams after interaction with the sample and reference. An output 342 of the detector circuit 340 is supplied to a computer or other control device. With use of a different optical device to create internal reflectance, sensitivity may be increased. Optical devices that produce multiple internal reflections may increase the sensitivity compared to the single reflection embodiment. The features of the FIG. 1 embodiment are otherwise applicable to FIG. 3, and accordingly the sensitivity of internal reflectance is enhanced by limiting the adverse effects of source noise and drift. In addition, the circuits of FIGS. 2A and 2B, and the general methods of the invention for noise cancellation also serve to increase sensitivity.

Figure 4:
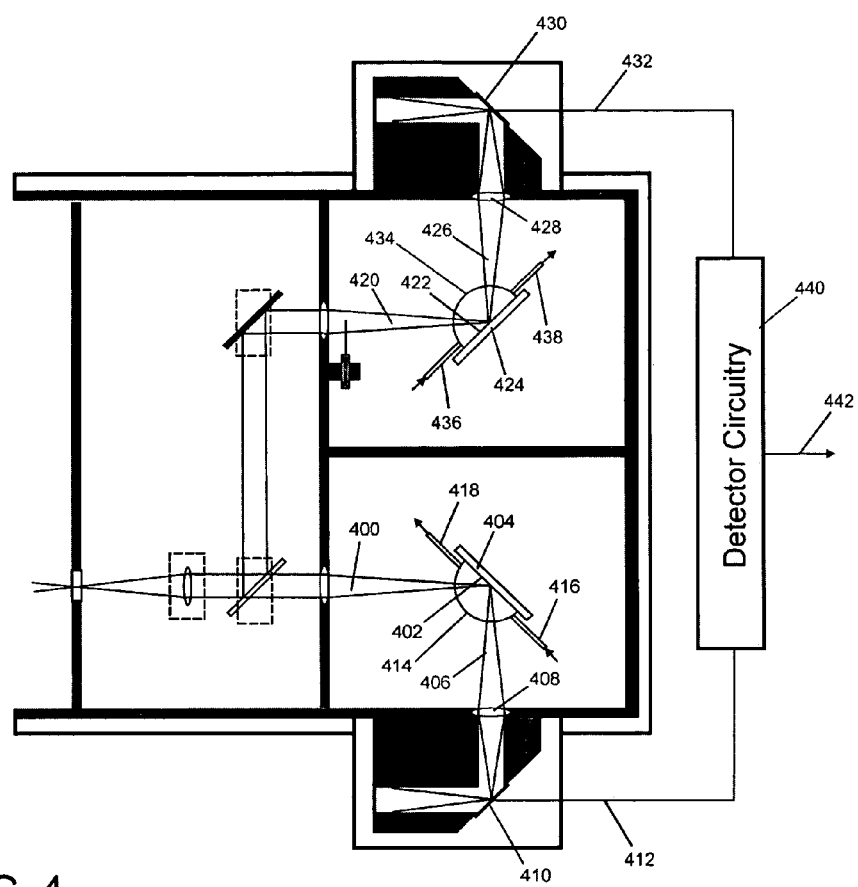
FIG. 4 illustrates a portion of a preferred embodiment specular reflection spectrophotometer.

FIG. 4 presents another modification of the FIG. 1 embodiment, and a method for measurement based upon specular reflectance. A sample beam 400 strikes a smooth reflective interaction surface 402, e.g., a mirror, of a wall 404. Interaction with a sample occurs at the interaction surface 402 and a reflected beam 406 is focused by a lens 408 onto a sample detector 410, e.g. a photodioide, mounted in a chamber including a light trap 411 at a non-perpendicular angle to the incoming beam. The detector 410 outputs its signal on a signal line 412. In FIG. 4, the angle of incidence with the interaction surface 402 and the angle of reflection from the surface are both 45° so that the specular reflection process changes the direction of the sample beam by a total of 90°, but this angle is an arbitrary choice as it was in the FIG. 3 embodiment. A sample cell includes an optically transparent closed interaction volume 414 that is sealed to and includes the wall 404 as part of the interaction volume 414. An inlet 416 and outlet 418 permit the introduction of sample into the interaction volume 414. The inlet and outlet are connected to positions outside the housing to allow the interaction volume 414 to be filled without opening the housing. The solid wall 404 forms one side of the interaction volume so that the reflective interaction surface 402 may be in contact with sample. In particular, it is of interest to study absorption of light by substances from the gas phase that are attracted to and held on the interaction surface 402.

A similar configuration is used for a reference cell. A sample beam 420 strikes a smooth reflective interaction surface 422, e.g., a mirror, of a wall 424. Interaction with a reference gas (or liquid) occurs at the interaction surface 422 and a reflected beam 426 is focused by a lens 428 onto a reference detector 430, e.g. a photodioide, mounted in a chamber including a light trap 431 in the same fashion that has been described previously. The reference detector 430 outputs its signal on a signal line 432. An optically transparent interaction volume 434 that is sealed to and includes the wall 424 as part of the interaction volume 434. An inlet 436 and outlet 438 permit the introduction of sample into the interaction volume 434. The inlet and outlet are connected to positions outside the housing (see FIG. 1 for housing) to allow the interaction volume 434 to be filled without opening the housing.

The sample beam is potentially attenuated (i) as it passes through the walls of interaction volume 414, (ii) as it passes through the gas sample held within the interaction volume and (iii) by striking the reflective interaction surface 402. The reference beam is also potentially attenuated (i) as it passes through the walls of the interaction volume 434, (ii) as it passes through the reference gas held within the interaction volume and (iii) by striking the reflective interaction surface 422. If the same gas is held within both interaction volumes 414 and 434, then the amount of light absorbed by the gas and by the cell walls per se will be identical for both sample and reference beams. The only potential difference in absorption will occur as the light beam strikes the two different interaction surfaces, 402 and 422.

The embodiment of FIG. 4 is especially useful if (i) the sample surface 402 has a strong tendency to interact with one or more components in the gas phase and (ii) the reference surface 422 has little or no tendency in interact with gas phase components. For example, the sample interaction surface 402 may be activated by chemical treatment, coated with antibodies or coated with specially formulated polymers. Such surface preparation will lead to strong interactions between the chemical species and the reflective surface, so that one or more targeted substances present in the gas phase can be captured on the sample interaction surface 402. The same substance(s) will not be captured on the reference interaction surface 422. If the substance(s) on interaction surface 402 absorb light, then the absorption can be used to detect and quantitate the absorbed substance(s).

The features of the FIG. 1 embodiment are otherwise applicable to FIG. 4, and accordingly the sensitivity of specular reflectance is enhanced by limiting the adverse effects of source noise and drift. In addition, the circuits of FIGS. 2A and 2B, and the general methods of the invention for noise cancellation also serve to increase sensitivity. The FIG. 4 embodiment allows both source noise cancellation to be accomplished and small amounts of light absorbed by species held on the surface to be measured. Thus, specular reflectance measurements can be used to monitor the structure of the sample surface where it can be used to detect and study physical and chemical properties of adsorbed molecular layers on the surface.

Figure 5:
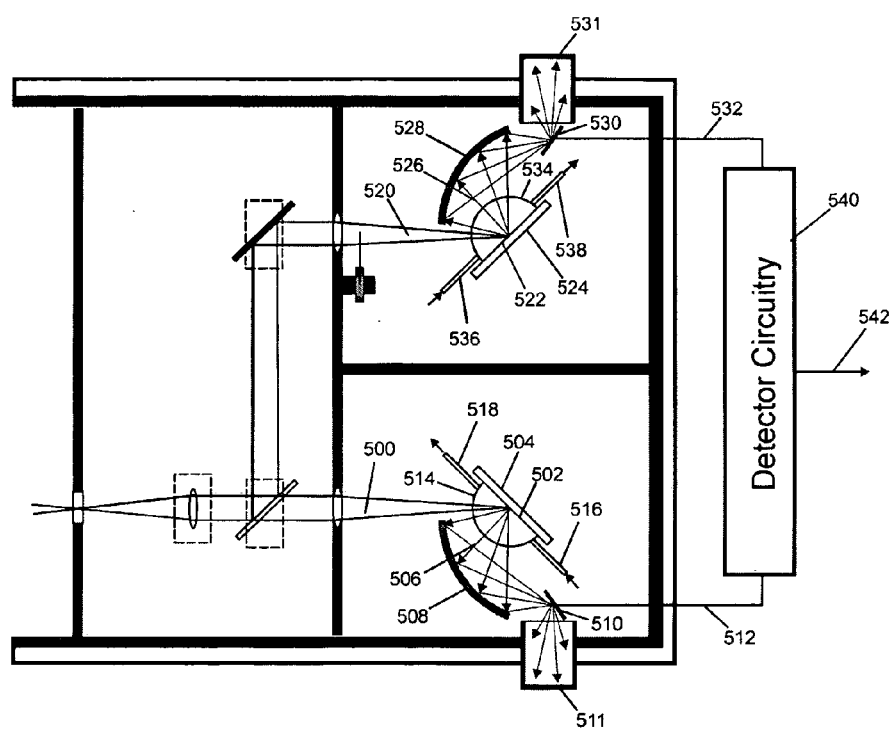
FIG. 5 illustrates a portion of a preferred embodiment diffuse reflection spectrophotometer.

FIG. 5 presents another modification of the FIG. 1 embodiment, and a method for measurement based upon diffuse reflectance. A sample beam 500 strikes a matte interaction surface 502 of a wall 504. Light is scattered over a range of directions, as indicated by arrows. A portion 506 of the scattered light is focused by a mirror 508 onto a sample detector 510, e.g., a photodiode, mounted in a chamber including a light trap 511. The sample detector signal is supplied on a signal line 512. A closed sample interaction volume 514 is completed on one side by the wall 504 so that sample supplied via inlet 516 and outlet 518 may interact with the interaction surface 502.

A reference cell is similarly constructed. A reference beam 520 strikes a matte interaction surface 522 of a wall 524. The light is scattered over a range of directions as indicated by arrows. A portion 526 of the scattered light is focused by mirror 528 onto a reference detector 530 mounted in a chamber including a light trap 531. The reference detector 530 outputs a signal on a signal line 532. A closed interaction volume 534 delivers reference to the interaction surface 525 and is supplied by an inlet 536 and outlet 538. A detector circuit 540 receives signals from the signal lines 512 and 532 and produces an output on signal line 542. In example embodiments the detector circuit 540 is constructed in accordance with either FIG. 2A or FIG. 2B. The output of signal lines 542 may be fed into a computer or other control device, for example.

As with the other embodiments, the methods for sensitivity increase applied above to enhance diffuse measurement. In all of the above embodiments, sample and reference detectors may be used to produce photocurrents that can be processed in ways to increase sensitivity. For example, taking the sample and reference photocurrent difference serves to suppress relatively fast random fluctuations of the light source. Effects of slower light source drift on peak heights can be compensated for by ratioing with the reference photocurrent. Thus, a function of the type given in Eq. 3 is the basis for quantitation in all the applications. For transmission measurements where the Beer-Lambert Law applies, Eq. 4 must be used. For all other applications, Eq. 3 can be used directly and the correlation between $V_D/V_R$ and analyte concentration must be determined empirically.

The cell inlets, outlets and bodies should also be chemically stable to most organic solvents if applied to a general purpose instrument, while specific purpose instruments may be tailored to be resistant to particular solvents. Teflon gaskets may serve as seals in the construction of the cells. Inlets and outlets should be filtered to prevent dust particles in the air from entering the system. In an automated instrument the flow of gas or fluid can be precisely controlled by a control system, which may include sensors to monitor, for example pressure, flow and temperature of the cells. Sensors should be chosen carefully to avoid introduction of thermal effects within the device. Flushing and filtering may be used with filtered inlet and outlet systems to remove dust particles, which would occur at the completion of device manufacture and also at the time of device set-up, for example. Following this, a closed system will remain clean if sample and reference materials are introduced through properly filtered inlets and outlets. The type of filtering system used will vary depending on whether gas or liquid samples are being analyzed, but many commercial filtering techniques are suitable.

Filtering liquid samples and references removes dust and particulates. However, in the case of liquids, bubbles and dissolved gases are also identified as potential contributors to noise. Another aspect of the invention deals with treatment to removed dissolved gases from liquid samples. This is accomplished by a degassing pre-treatment of the liquid prior to entering the sample cell, e.g., an ultrasonic treatment. Preferably, in practice of the invention for liquids samples, both the solvent and the analytical solution are degassed. The degassing removes dissolved gases. Generally, bubbles will not be an issue with the sample cell when liquids are delivered in a closed system. However, the degassing would also remove bubbles.

Unitary housing construction can provide a compact, mechanically and thermally stable device in accordance with the invention and apply any of the types of measurement discussed above. Exemplary embodiments will be discussed to illustrate additional preferred features of the invention. FIG. 6 shows a preferred embodiment with a unitary housing. Thermal stabilization in the FIG. 6 embodiment is achieved primarily from a unitary solid metal housing 600. A material having a high heat conductivity, e.g. Aluminum, is used. A hollowed portion 600a is carved out in a shape and depth to provide for the mounting and placement of device components. A cover plate (not shown) of solid metal seals the housing 600, which is insulated on all sides, including the cover plate. Excellent mechanical stability is also provided by the unitary structure of the housing 600. The solid unitary metal housing can provide relatively large thermal mass in a compact package, permitting a smaller device than in the case of the FIG. 1 embodiment. In FIG. 6, spacing between optical components is exemplary, while the unitary housing permits shrinking the optical path length while still attaining the thermal stability of the invention. The thermal drift of an experimental transmissive device having a unitary body of the nature of FIG. 6 was found to be <0.0005° C./min.

Monochromatic light from a monochromator is coupled into the housing 600 through an optical fiber 601 and an aperture 602. The beam 603 passes through a collimating lens 604, and the collimated beam 605 strikes a beam splitter 606 at an angle of incidence of 45° to produce a transmitted beam 607 and a reflected beam 608. The beam 607 strikes a second beam splitter 610 at an angle of incidence of 45° to produce a transmitted beam 611 and a reflected beam 612. Beam splitter 610 is identical to 606. The beam 611 becomes trapped in light trap 613. Similarly the beam 608 strikes the third identical beam splitter 614 at angle of incidence of 45°, which produces a transmitted beam 615 and a reflected beam 616. The walls 600b are machined to precisely mount the splitters 606, 610 and 614 at the angle of incidence of 45°. The beam 616 becomes trapped in light trap 617. At this point, the two beams 612 and 615 should be well matched (identical phase, intensity, and polarization). This beam splitting arrangement obtains the matched beams over a broad wavelength region from UV to far IR. The beams then pass through focusing lenses 618 and 619, which focus the beams 620 and 621 at a sample cell indicated generally at 622 (constructed for total internal reflection in accordance with FIG. 3, including surfaces, closed volumes, inlets, outlets, etc. as shown in FIG. 3) and a reference cell indicted generally at 623 (also constructed for total internal reflection in accordance with FIG. 3). The beams, after interaction with sample and reference exit respective prisms 622a and 623a, are refocused through lenses 624 and 625, and enter detector chambers 626 and 627, where detectors 628 and 629 output signals on signal lines 630 and 631 to a detector circuit 632. Beam splitters are preferably mounted on the wall structure 600b of the solid metal housing 600. Lenses are held in holders mounted to the base plate. This provides thermal and mechanical stability. Another option is to provide predefined slots as part of the hollowed portion 600a, e.g., in walls 600b to mount lenses. Beams reflected from the detector surfaces enter regions 633 and 634 of the detector chamber, where they are trapped. The use of three beam splitters in the preferred embodiment results in the loss of more than half the initial light power. The exact amount depends upon the beam splitter characteristics. To minimize the light loss, commercially available beam splitters with 50/50 (T/R) splitting ratio should be used. Despite the loss of light, the configuration has the great advantage that with three matched beam splitters, the two emergent beams will be of equal power at all wavelengths, i.e., $P_{615}=P_{605} R_{606} T_{614}$ and $P_{612}=P_{605} T_{606} R_{610}$, where reflected fractions, $R_{606}=R_{610}=R_{614}$ and transmitted fractions, $T_{606}=T_{610}=T_{614}$. The beams also have equal polarization and phase at all wavelengths. This greatly simplifies the problem of balancing the beams. Preliminary measurements and calculations made by us indicate that under realizable conditions (machining tolerances and commercial beam splitters), the beam powers will differ by much less than 0.5% over the entire range of wavelength from UV to far IR, which is sufficient to ensure source noise cancellation to well below the shot noise limit. All preferred detector circuits shown in FIG. 2 will function very well with beams of identical power.

Mirror prisms, which are available commercially, could be used in the FIG. 6 embodiment as an alternative to use of the three beam splitter configuration. With a mirror prism, a collimated light beam is divided by reflections from the two-mirrored surfaces of the prism into two beams of nominally equal power. The two beams diverge by 180° so that they must be redirected by reflections from two additional mirrors to become parallel. Because of potential scattering of light by the apex, that region of the Mirror Prism is usual shielded from the light beam. The power ratio of the beams can be adjusted by moving the prism or with appropriately placed apertures. However, based on our experience, we believe that this configuration is more susceptible to thermal drift than is the three Beam Splitter configuration.

Another preferred embodiment with a substantially solid unitary housing is shown in FIG. 7. The FIG. 7 embodiment is similar to the FIG. 6 embodiment, having a solid housing 700 with hollowed portion 700a shaped for component placement and wall structure 700b for beam splitter mounting, and possessing the superior optical stability features of the FIG. 6 embodiment, but the FIG. 7 embodiment uses diffuse reflection from a matte surface as in FIG. 5. A light source 702 in FIG. 7 is, for example a laser with optics to produce beam, and the three beam splitter arrangement of FIG. 6 is achieved with beam splitters 704, 706 and 708. Sample and reference cells are indicated generally at 710 and 712, and are constructed in accordance with FIG. 5 (refer to FIG. 5 for details including matte surfaces, walls, volumes, mirrors, inlets, outlets, etc.).

While various embodiments of the present invention have been shown and described, it should be understood that other modifications, substitutions, and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A spectrophotometer, comprising:
   a sealed housing lacking an internal light source;
   a reference cell mounted in said housing;
   a sample cell mounted in said housing;
   an optical system within the housing to split an externally generated light beam into reference and sample beams and to deliver the reference and sample beams through separate paths, one path passing the reference beam into the reference cell and another path passing the sample beam into said sample cell;
   reference cell interaction means for interacting the reference beam with a reference and reflecting at least a portion of the reference beam;
   sample cell interaction means for interacting the sample beam with a sample and reflecting at least a portion of the sample beam;
   a reference light detector for detecting at least a portion of light reflected by said reference cell interaction means;
   a sample light detector for detecting at least a portion of light reflected by said sample cell interaction means;
   a light guide for delivering the externally generated light beam into said optical system from a light source external to said sealed housing; and
   a detector circuit receiving a reference current from said reference light detector and a sample current from said sample light detector, said detector circuit producing a difference voltage proportional to the difference between the reference current and the sample current by a current mode subtraction at a summing point having feedback to balance said reference current and said sample current to produce a difference current that is then converted to the difference voltage,
   said detector circuit simultaneously producing the difference voltage and at least one of a voltage proportional to said reference current and a voltage proportional to said sample current.

2. The spectrophotometer of claim 1, further comprising a sealed mount mounting said light guide to said housing.

3. The spectrophotometer of claim 1, wherein the light source external to said housing is optically coupled to said light guide.

4. The spectrophotometer according to claim 1, further comprising a selective wavelength device optically coupled to said light guide.

5. The spectrophotometer according to claim 4, wherein said selective device comprises an interference filter.

6. The spectrophotometer of claim 1, wherein said reference cell interaction means and said sample cell interaction means each utilize total internal reflection to respectively interact the reference beam with the reference and the sample beam with the sample.

7. The spectrophotometer of claim 1, wherein said reference cell interaction means and said sample cell interaction means each utilize specular reflection to respectively interact the reference beam with the reference and the sample beam with the sample.

8. The spectrophotometer of claim 1, wherein said reference cell interaction means and said sample cell interaction means each utilize diffuse reflection to respectively interact the reference beam with the reference and the sample beam with the sample.

9. The spectrophotometer according to claim 1, further comprising a dielectric beam splitter for splitting the externally generated light beam into separate sample and reference beams emergent on the two paths.

10. The spectrophotometer according to claim 1, further comprising passive thermal stabilization means for promoting internal thermal equilibrium.

11. The spectrophotometer according to claim 1, wherein said reference current is converted to a reference voltage and said sample current is converted to a sample voltage, said reference and sample voltages are subtracted at an input to a difference amplifier, said difference amplifier then producing the difference voltage.

12. The spectrophotometer according to claim 11, wherein said detector circuit further comprises a feedback loop to feed a small fraction of a smaller one of said sample current and said reference current to said input to said difference amplifier.

13. The spectrophotometer according to claim 12, wherein said small fraction of said smaller one of said sample and said reference current is an amount to produce an approximate $10^{-3}$ or less imbalance between said sample current and said reference.

14. The spectrophotometer according to claim 1, wherein said housing comprises a solid unitary metal housing having a hollowed portion shaped to provide for mounting and placement of said reference cell, said sample cell, said optical system, said reference light detector, and said sample light detector.

15. The spectrophotometer according to claim 14, further comprising slots in said solid unitary metal housing for holding components of said optical system.

16. The spectrophotometer according to claim 14, wherein said solid unitary metal housing comprises Aluminum.

17. A spectrophotometer, comprising:
a sealed housing lacking an internal light source;
a reference cell mounted in said housing;
a sample cell mounted in said housing;
an optical system within the housing to split an externally generated light beam into reference and sample beams and to deliver the reference and sample beams through separate paths, one path passing the reference beam into the reference cell and another path passing the sample beam into said sample cell;
reference cell interaction means for interacting the reference beam with a reference and reflecting at least a portion of the reference beam;
sample cell interaction means for interacting the sample beam with a sample and reflecting at least a portion of the sample beam;
a reference light detector for detecting at least a portion of light reflected by said reference cell interaction means;
a sample light detector for detecting at least a portion of light reflected by said sample cell interaction means;
a light guide for delivering the externally generated light beam into said optical system from a light source external to said sealed housing;
a sample light detector chamber to house said sample light detector;
a reference light detector chamber to house said reference light detector; and
light traps in each of said sample light detector chamber and said reference light detector chamber to trap light reflected from said sample light detector and said reference light detector, respectively.

18. A spectrophotometer, comprising:
a substantially solid thermally conductive housing;
a hollow portion in said housing defining light communication paths and component locations;
a light entry aperture in optical communication with said hollow portion;
a collimating lens in optical communication with said light entry aperture;
a first beam splitter in optical communication with said collimating lens;
a second beam splitter in optical communication with a transmissive side of said first beam splitter;
a third beam splitter in optical communication with a reflective side of said first beam splitter;
a reference cell reflection interaction interface and reflected beam detection system in optical communication with one of said second and third beam splitters; and
a sample cell reflection interaction interface and reflected beam detection system in optical communication with the other of said second and third beam splitters.

19. The spectrophotometer according to claim 18, wherein said reference and said sample cell interaction interfaces and reflected beam detection systems are in optical communication with a reflective side of said second beam splitter and a transmissive side of said third beam splitter.

20. The spectrophotometer according to claim 18, further comprising light traps formed as part of said hollow portion and disposed to trap light transmitted from the second beam splitter and reflected light from said third beam splitter.

21. The spectrophotometer according to claim 18, further comprising additional light traps to trap reflected light from said reference and sample cell and detection systems.

22. The spectrophotometer according to claim 18, wherein said reference cell reflection interaction interface and reflected beam detection system and said sample cell reflection interaction interface and reflected beam detection system each comprise:
a prism including an interaction surface;
a detector;
a lens that focuses a beam output from said prism onto said detector; and
a closed interaction volume having an inlet and an outlet for delivering gas or liquid to the interaction surface.

23. The spectrophotometer according to claim 18, wherein said reference cell reflection interaction interface and reflected beam detection system and said sample cell reflection interaction interface and reflected beam detection system each comprise:
a reflective interaction surface;
a detector;
a lens that focuses a beam output from said reflective interaction surface onto said detector; and
a closed interaction volume having an inlet and an outlet for delivering gas or liquid to the reflective interaction surface.

24. The spectrophotometer according to claim 18, wherein said reference cell reflection interaction interface and reflected beam detection system and said sample cell reflection interaction interface and reflected beam detection system each comprise:
a matte interaction surface;
a detector;

a lens or mirror that focuses scattering output from said matte interaction surface onto said detector; and a closed interaction volume having an inlet and an outlet for delivering gas or liquid to the interaction surface.

25. A spectrophotometer, comprising:

a sealed housing lacking an internal light source;

a reference cell mounted in said housing;

a sample cell mounted in said housing;

an optical system within the housing to split an externally generated light beam into reference and sample beams and to deliver the reference and sample beams through separate paths, one path passing the reference beam into the reference cell and another path passing the sample beam into said sample cell;

a reference cell reflection interaction interface and reflected beam detection system in optical communication with the one path passing the reference beam;

a sample cell reflection interaction interface and reflected beam detection system in optical communication with the another path passing the sample beam, wherein said reference cell reflection interaction interface and reflected beam detection system and said sample cell reflection interaction interface and reflected beam detection system each comprise:

a prism including an interaction surface;

a detector;

a lens or mirror that focuses a beam output from said prism onto said detector; and a closed interaction volume having an inlet and an outlet for delivering gas or liquid to the interaction surface;

a reference light detector for detecting at least a portion of light reflected by said reference cell interaction means;

a sample light detector for detecting at least a portion of light reflected by said sample cell interaction means; and a light guide for delivering the externally generated light beam into said optical system from a light source external to said sealed housing.

26. A spectrophotometer, comprising:

a sealed housing lacking an internal light source;

a reference cell mounted in said housing;

a sample cell mounted in said housing;

an optical system within the housing to split an externally generated light beam into reference and sample beams and to deliver the reference and sample beams through separate paths, one path passing the reference beam into the reference cell and another path passing the sample beam into said sample cell;

a reference cell reflection interaction interface and reflected beam detection system in optical communication with the one path passing the reference beam;

a sample cell reflection interaction interface and reflected beam detection system in optical communication with the another path passing the sample beam, wherein said reference cell reflection interaction interface and reflected beam detection system and said sample cell reflection interaction interface and reflected beam detection system each comprise:

a reflective interaction surface;

a detector;

a lens that focuses a beam output from said reflective interaction surface onto said detector; and a closed interaction volume having an inlet and an outlet for delivering gas or liquid to the reflective interaction surface;

a reference light detector for detecting at least a portion of light reflected by said reference cell interaction means;

a sample light detector for detecting at least a portion of light reflected by said sample cell interaction means; and a light guide for delivering the externally generated light beam into said optical system from a light source external to said sealed housing.

27. The spectrophotometer according to claim 26, wherein said housing comprises:

a substantially solid thermal conductive housing; and a hollow portion in said housing defining light communication paths and component locations.

28. A spectrophotometer, comprising:

a sealed housing lacking an internal light source;

a reference cell mounted in said housing;

a sample cell mounted in said housing;

an optical system within the housing to split an externally generated light beam into reference and sample beams and to deliver the reference and sample beams through separate paths, one path passing the reference beam into the reference cell and another path passing the sample beam into said sample cell;

a reference cell reflection interaction interface and reflected beam detection system in optical communication with the one path passing the reference beam;

a sample cell reflection interaction interface and reflected beam detection system in optical communication with the another path passing the sample beam, wherein said reference cell reflection interaction interface and reflected beam detection system and said sample cell reflection interaction interface and reflected beam detection system each comprise:

a matte interaction surface;

a detector;

a lens that focuses scattering output from said matte interaction surface onto said detector; and a closed interaction volume having an inlet and an outlet for delivering gas or liquid to the interaction surface a reference light detector for detecting at least a portion of light reflected by said reference cell interaction means;

a sample light detector for detecting at least a portion of light reflected by said sample cell interaction means; and a light guide for delivering the externally generated light beam into said optical system from a light source external to said sealed housing.

* * * * *